(12) United States Patent
Brunner et al.

(10) Patent No.: US 11,066,553 B2
(45) Date of Patent: Jul. 20, 2021

(54) IMIDAZOYL UREA POLYMERS AND THEIR USE IN METAL OR METAL ALLOY PLATING BATH COMPOSITIONS

(71) Applicant: Atotech Deutschland GmbH, Berlin (DE)

(72) Inventors: Heiko Brunner, Berlin (DE); Lars Kohlmann, Berlin (DE); Agnieszka Witczak, Berlin (DE); Olivier Mann, Berlin (DE)

(73) Assignee: Atotech Deutschland GmbH, Berlin (DE)

( * ) Notice: Subject to any disclaimer, the term of this patent is extended or adjusted under 35 U.S.C. 154(b) by 0 days.

(21) Appl. No.: 15/748,203

(22) PCT Filed: Aug. 19, 2016

(86) PCT No.: PCT/EP2016/069683
§ 371 (c)(1),
(2) Date: Jan. 29, 2018

(87) PCT Pub. No.: WO2017/036816
PCT Pub. Date: Mar. 9, 2017

(65) Prior Publication Data
US 2019/0144667 A1    May 16, 2019

(30) Foreign Application Priority Data
Aug. 31, 2015 (EP) .................................... 15183118

(51) Int. Cl.
*C08L 75/02* (2006.01)
*C08G 71/02* (2006.01)
*C25D 3/38* (2006.01)
*C07C 275/22* (2006.01)
*C07D 233/61* (2006.01)

(52) U.S. Cl.
CPC ............ *C08L 75/02* (2013.01); *C07C 275/22* (2013.01); *C07D 233/61* (2013.01); *C08G 71/02* (2013.01); *C25D 3/38* (2013.01)

(58) Field of Classification Search
CPC ........... C08L 75/02; C25D 3/38; C08G 71/02; C07C 275/22; C07D 233/61
See application file for complete search history.

(56) References Cited

U.S. PATENT DOCUMENTS

| | | | |
|---|---|---|---|
| 4,157,388 A | 6/1979 | Christiansen | |
| 5,976,341 A | 11/1999 | Schumacher et al. | |
| 6,099,711 A | 8/2000 | Dahms et al. | |
| 7,109,375 B2 | 9/2006 | Herdman et al. | |
| 8,066,864 B2 | 11/2011 | Jimenez et al. | |
| 8,268,158 B2 | 9/2012 | Niazimbetova et al. | |
| 8,357,764 B2 | 1/2013 | Foo et al. | |
| 8,679,316 B2 | 3/2014 | Brunner et al. | |
| 9,307,369 B2 | 4/2016 | Nakata et al. | |
| 9,388,308 B2 | 7/2016 | Okamoto et al. | |
| 9,506,158 B2 | 11/2016 | Rohde et al. | |
| 9,551,080 B2 | 1/2017 | Brunner et al. | |
| 2004/0187731 A1 | 9/2004 | Wang et al. | |
| 2008/0262063 A1* | 10/2008 | Buchholz | A61P 25/00 514/394 |
| 2009/0205969 A1 | 8/2009 | Jimenez et al. | |
| 2010/0280192 A1* | 11/2010 | Foo | C07D 233/61 525/529 |
| 2010/0280211 A1* | 11/2010 | Foo | C08G 59/5073 528/59 |
| 2011/0290660 A1* | 12/2011 | Niazimbetova | C07D 233/60 205/297 |
| 2012/0160698 A1* | 6/2012 | Brunner | C08G 71/02 205/244 |
| 2013/0316190 A1 | 11/2013 | Bedrnik et al. | |

FOREIGN PATENT DOCUMENTS

| | | | |
|---|---|---|---|
| CN | 102414241 A | 4/2012 | |
| CN | 103572334 A | 2/2014 | |
| CN | 103952733 A | 7/2014 | |
| CN | 104746081 A | 7/2015 | |
| EP | 2735627 A1 | 5/2014 | |
| JP | 2001152083 A | 6/2001 | |
| JP | 2010180162 | 8/2010 | |
| JP | 2011084821 A | 4/2011 | |
| JP | 2013014833 A | 1/2013 | |
| TW | 201038612 A1 | 11/2010 | |
| WO | WO-2010122995 A1 * | 10/2010 | ............ C08L 63/00 |

OTHER PUBLICATIONS

PCT/EP2016/069683; PCT International Search Report and Written Opinion of the International Searching Authority dated Sep. 27, 2016.
Search Report for Taiwanese Patent Application No. 105126562 dated Oct. 14, 2019.
Dong Wan Seo et al.; "Synthesis of acetyl imidazolium-based electyrolytes and application for dye-sensitized solar cells"; Electrochimica Acta 57 (2011); pp. 285-289.
Office Action for Chinese Patent Application No. 201680050385.X dated May 7, 2020.

* cited by examiner

*Primary Examiner* — Rabon A Sergent
(74) *Attorney, Agent, or Firm* — Renner, Otto, Boisselle & Sklar, LLP

(57) ABSTRACT

The present invention relates to imidazoyl urea polymers and their use in aqueous acidic plating baths for metal or metal alloy deposition such as electrolytic deposition of copper or alloys thereof in the manufacture of printed circuit boards, IC substrates, semiconducting and glass devices for electronic applications. The plating bath according to the present invention comprises at least one source of metal ions and an imidazoyl urea polymer. The plating bath is particularly useful for filling recessed structures and build-up of pillar bump structures.

21 Claims, No Drawings

IMIDAZOYL UREA POLYMERS AND THEIR USE IN METAL OR METAL ALLOY PLATING BATH COMPOSITIONS

The present application is a U.S. National Stage Application based on and claiming benefit and priority under 35 U.S.C. § 371 of International Application No. PCT/EP2016/069683, filed 19 Aug. 2016, which in turn claims benefit of and priority to European Application No. 15183118.7 filed 31 Aug. 2015, the entirety of both of which is hereby incorporated herein by reference.

FIELD OF THE INVENTION

The invention relates to imidazoyl urea polymers and plating bath compositions for metal or metal alloy deposition comprising said polymers as additives. It particularly relates to imidazoyl urea polymers as additives in electrolytic deposition of copper or copper alloys. The plating bath compositions are suitable in the manufacture of printed circuit boards, IC substrates and the like as well as for metallisation of semiconducting and glass substrates.

BACKGROUND OF THE INVENTION

Aqueous acidic plating baths for electrolytic deposition of copper are used for manufacturing printed circuit boards and IC substrates where fine structures like trenches, through holes (TH), blind micro vias (BMV) and pillar bumps need to be filled or build up with copper. Another application of such electrolytic deposition of copper is filling of recessed structures such as through silicon vias (TSV) and dual damascene plating or forming redistribution layers (RDL) and pillar bumps in and on semiconducting substrates. Still another application which is becoming more demanding is filling through glass vias, i.e. holes and related recessed structures in glass substrates with copper or copper alloys by electroplating.

Conventionally, a combination of various additives is used in aqueous plating bath compositions. For example, electrolytic copper plating baths comprise a multitude of individual additives including levellers, carrier-suppressors and accelerator-brighteners. Similarly, zinc plating baths contain additives to improve inter alia the visual properties of zinc deposits.

The patent application EP 1 069 211 A2 discloses aqueous copper plating bath s comprising a source of copper ions, an acid, a carrier additive, a brightener additive and a leveller additive which can be poly[bis(2-chloroethyl)ether-alt-1,3-bis[3-(dimethylamino)propyl]urea (CAS-No. 68555-36-2) which contains an organo-bound halide atom (e.g., covalent C—Cl bonds) in at least one terminus.

US 2009/0205969 A1 describes cross-linked polymers made from urea, N,N dialkylaminoalkylamine and N,N-bis-(aminoalkyl)-alkylamine as additive for electrolytic metal deposition. The process disclosed therein relates to electrolytic zinc deposition.

Similar urea-based polymers are also reported in U.S. Pat. No. 4,157,388 wherein all urea moieties are bridged via nitrogen containing alkylenes, i.e. secondary, tertiary amines and the like. Cationic derivatives and their use in electrolytic plating bath are disclosed in the German patent application DE 10 2005 060 030 A1. The individual urea moieties in these polymers are linked by quarternary ammonium derivatives.

Ureyl polymers are known in the art from EP 2 735 627 A1 as levellers for the electrolytic deposition of copper. Such polymers are can be obtained by a polyaddition of aminourea derivatives and nucleophiles. WO 2011/029781 teaches the same polymers for the electrolytic deposition of zinc. The latter document also teaches bisurea derivatives of a general formula without disclosing any specific examples. Moreover, the examples relating to said structures are diamides (examples 5 and 18 therein).

However, such additives when used in acidic copper plating baths are not suitable to fulfil the current and future requirements in manufacture of advanced printed circuit boards, IC substrates and metallisation of semiconducting and glass substrates. Depending on the circuitry layout, BMVs' in printed circuit boards and IC substrates need to be filled with copper not only conformally but completely. Typical requirements for BMV filling are for example: obtaining a completely filled BMV while depositing no more than 12 to 18 μm of copper onto the neighbouring planar substrate areas and at the same time creating a dimple on the outer surface of the filled BMV of no more than 5 μm.

In metallisation of semiconducting wafers, TSV filling must lead to a complete and void-free filling with copper while creating no more than 1/5 of via diameter of overplated copper onto the neighbouring planar areas. Similar requirements are demanded for filling through glass vias with copper.

OBJECTIVE OF THE INVENTION

Thus, it is an objective of the present invention to provide an aqueous metal or metal alloy plating bath, preferably a copper plating bath for electrolytic deposition of copper or copper alloys, which fulfils the requirements for the above mentioned applications in the field of printed circuit board and IC substrate manufacturing as well as metallisation of semiconducting substrates like TSV filling, dual damascene plating, deposition of redistribution layers or pillar bumping and filling of through glass vias.

SUMMARY OF THE INVENTION

These objectives are solved by using an imidazoyl urea polymer according to claim 1 as additive in an aqueous metal or metal alloy plating bath, preferably in a copper plating bath for electrolytic deposition of copper or copper alloys.

These objectives are also solved by using the dual-functional imidazoyl urea polymer according to claim 1 as as both leveller and carrier-suppressor in an aqueous metal or metal alloy plating baths such as plating baths for electrolytic deposition of copper or copper alloys.

These objectives are further solved by the inventive aqueous metal or metal alloy plating bath comprising a source of metal ions characterised in that it comprises at least one imidazoyl urea polymer according to claim 1.

Recessed structures such as trenches, blind micro vias (BMVs'), through silicon vias (TSVs') and through glass vias can be filled with metal or metal alloys, preferably with copper or copper alloys deposited from the aqueous copper plating bath according to the present invention. The filled recessed structures are void-free and have an acceptable dimple, i.e., a planar or an almost planar surface. Furthermore, the build-up of pillar bump structures is feasible.

The inventive aqueous metal or metal alloy, preferably copper or copper alloy, plating bath allows for uniform filling of recessed structures, in particular when recessed structures having different aspect ratios are filled in one step.

DETAILED DESCRIPTION OF THE INVENTION

The inventive imidazoyl urea polymer comprises a polymeric building block according to formula (I)

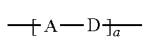  (I)

wherein A represents a unit derived from a urea compound of the following formulae (A1) and (A2)

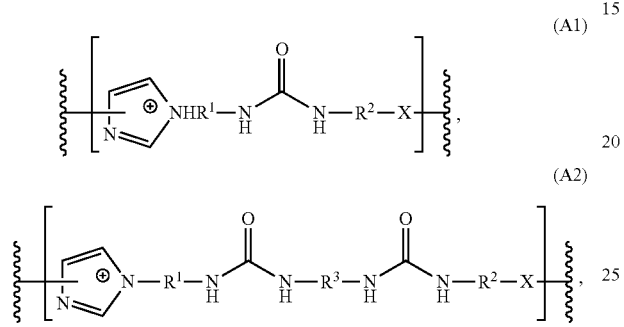

wherein
X is a divalent residue selected from the group consisting of

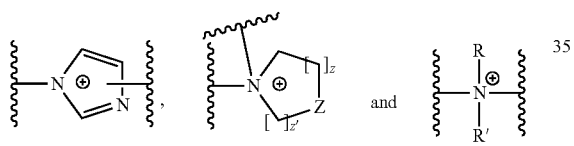

wherein Z is selected from —$CH_2$—, O, S; z and z' are integers independently ranging from 1 to 6, preferably 1 to 3; R and R' are monovalent residues each selected independently from the group consisting of hydrogen, alkyl, aryl, aralkyl and —$CH_2$—$CH_2$—$(OCH_2CH_2)_y$—OH wherein y is an integer from 1 to 4, preferably selected from methyl, ethyl, hydroxyethyl or —$CH_2CH_2(OCH_2CH_2)_y$—OH, wherein y is an integer from 1 to 4; X preferably is

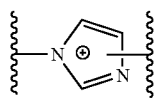

as this facilitates the overall synthesis of the imidazoyl urea polymers according to the invention;

$R^1$ and $R^2$ are divalent residues each selected independently from the group consisting of —$(CH_2)_b$— and —$(CH_2)_c$—$[CH(R^4)$—$CH_2$—$O]_d$—$(CH_2)_e$— wherein b is an integer from 2 to 12, b preferably is an integer ranging from 2 to 3; c is an integer ranging from 0 to 3; d is an integer ranging from 1 to 100, d preferably ranges from 1 to 20; e is an integer ranging from 1 to 3; each $R^4$ is independently from each other selected from the group consisting of alkyl, aryl and hydrogen, preferably it is selected from $C_1$- to $C_6$-alkyl, phenyl and hydrogen, more preferably it is selected from hydrogen, methyl, ethyl, propyl, even more preferably it is selected from hydrogen and methyl, most preferably $R^1$ and $R^2$ are selected from 1,2-ethylene (—$CH_2$—$CH_2$—), 1,3-propylene (—$CH_2$—$CH_2$—$CH_2$—), —$(CH_2)_2$—O—$(CH_2)_2$— and —$(CH_2)_2$—O—$(CH_2)_2$—O—$(CH_2)_2$— group;

$R^3$ is a divalent residue which is selected from the group consisting of alkylene, arylene and —$(CH_2)_f$—$[CH(R^5)$—$CH_2$—$O]_g$—$(CH_2)_h$—, wherein f is an integer ranging from 0 to 3; g is an integer ranging from 1 to 100, g preferably ranges from 1 to 20; h is an integer ranging from 1 to 3; each $R^5$ is independently from each other selected from the group consisting of alkyl, aryl and hydrogen, preferably it is selected from $C_1$- to $C_6$-alkyl, phenyl and hydrogen, more preferably it is selected from hydrogen, methyl, ethyl, propyl, even more preferably it is selected from hydrogen and methyl, most preferably $R^3$ is selected from 1,2-ethylene (—$CH_2$—$CH_2$—), 1,3-propylene (—$CH_2$—$CH_2$—$CH_2$—), —$(CH_2)_2$—O—$(CH_2)_2$—, $(CH_2)_2$—O—$(CH_2)_2$—O—$(CH_2)_2$— and —$(CH_2)_2$—O—$(CH_2)_2$—O—$(CH_2)_2$— group;

a is an integer and ranges from 1 to 40, more preferably it ranges from 3 to 30, most preferably it ranges from 5 to 20; and D is a divalent residue and is selected from the group consisting of —$CH_2$—CH(OH)—$CH_2$—, —$CH_2$—CH(SH)—$CH_2$—, —$(CH_2)_i$—$[CH(R^6)$—$CH_2$—$O]_j$—$(CH_2)_k$— and —$CH_2$—CH(OH)—$(CH_2)_l$—$[CH(R^7)$—$CH_2$—$O]_m$—$(CH_2)_n$—CH(OH)—$CH_2$—, preferably from —$CH_2$—CH(OH)—$CH_2$—, —$(CH_2)_i$—$[CH(R^6)$—$CH_2$—$O]_j$—$(CH_2)_k$— and —$CH_2$—CH(OH)—$(CH_2)_l$—$[CH(R^7)$—$CH_2$—$O]_m$—$(CH_2)_n$—CH(OH)—$CH_2$— wherein i is an integer ranging from 0 to 3; j is an integer ranging from 1 to 100, j preferably ranges from 1 to 20; k is an integer ranging from 1 to 3; each $R^6$ is independently from each other selected from the group consisting of alkyl, aryl and hydrogen, preferably it is selected from $C_1$- to $C_6$-alkyl, phenyl and hydrogen, more preferably it is selected from hydrogen, methyl, ethyl, propyl, even more preferably it is selected from hydrogen and methyl; l is an integer ranging from 1 to 3; m is an integer ranging from 1 to 100, m preferably ranges from 1 to 20; n is an integer ranging from 1 to 3; each $R^7$ is independently from each other selected from the group consisting of alkyl, aryl and hydrogen, preferably it is selected from $C_1$- to $C_6$-alkyl, phenyl and hydrogen, more preferably it is selected from hydrogen, methyl, ethyl, propyl, even more preferably it is selected from hydrogen and methyl;

wherein the individual units A may be the same or different, wherein the individual units D may be the same or different.

In a particularly preferred embodiment of the present invention D is —$(CH_2)_o$—$[CH(R^8)$—$CH_2$—$O]_p$—$(CH_2)_q$— and even more preferred o is 0 and p is an integer ranging from 1 to 100 and q is an integer ranging from 1 to 3.

Preferably, the inventive imidazoyl urea polymer comprises a polymeric building block according to formula (I) wherein A is selected to be one or more units derived from formula (A1). Particularly, X is selected to be

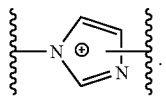

In one preferential embodiment of the present invention $R^1$, $R^2$ and $R^3$ are free of nitrogen atoms.

The imidazoyl urea polymers are obtainable by a reaction of one or more monomer urea compounds according to formulae (A1') and/or (A2') and one or more monomers B selected from the group consisting of (B1), (B2), (B3) and/or (B4), whereof (B1), (B2), (B3) are preferred, each of which are represented by the following formulae

E-G$^1$-E (B1),

E-G$^2$-R$^9$ (B2) and

(B3)

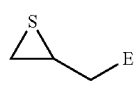
(B4)

wherein
G$^1$ and G$^2$ are divalent residues represented by the following formula —(CH$_2$)$_r$—[CH(R$^{10}$)—CH$_2$—O]$_s$—(CH$_2$)$_t$— wherein r is an integer ranging from 0 to 3; s is an integer ranging from 1 to 100, s preferably ranges from 1 to 20; t is an integer ranging from 1 to 3; each R$^{10}$ is independently from each other selected from the group consisting of alkyl, aryl and hydrogen, preferably it is selected from C$_1$- to C$_6$-alkyl, phenyl and hydrogen, more preferably it is selected from hydrogen, methyl, ethyl, propyl, even more preferably it is selected from hydrogen and methyl;
E each represent leaving groups individually selected from triflate, nonaflate, alkylsulphonates such as methanesulphonate, arylsulphonates such as tosylate, phenylsulphonate, p-nitrobenzosulphonate, p-bromobenzosulphonate and halogenides such as chloride, bromide and iodide; and
R$^9$ is a monovalent residue selected from the group consisting of C$_1$- to C$_8$-alkyl, C$_1$- to C$_8$-alkenyl, aralkyl, aryl, R$^9$ preferably is selected from methyl, ethyl, propyl and allyl.

The linkages between urea compounds A according to formulae (A1) and/or (A2) and monomers B1 to B3 occur via one of the nitrogen atoms in the imidazoyl moieties in the urea compounds. It is possible that these linkages occur via any of the nitrogen atoms present in the imidazoyl moieties. However, the inventors found a slight regioselectivity for the linkage via the nitrogen atom bonded to R$^1$ and/or R$^2$ (see preparation example 8). If X in (A1) and/or (A2) is chosen to be

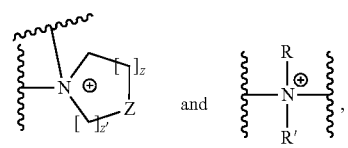

then, the linkages can also occur via the nitrogen atoms present in these groups forming for example quaternary ammonium moieties (depending e.g. on the residues R and R').

The units A represented by the formulae (A1) and (A2) are derived from the monomer urea compounds of the following formulae (A1') and (A2')

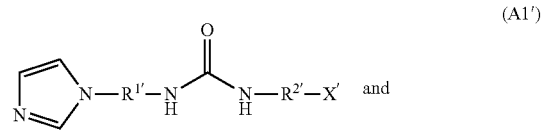
(A1')

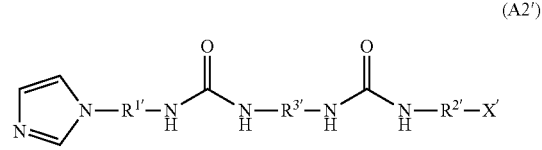
(A2')

which are used to synthesize the imidazoyl urea polymer according to the invention.

X' is a monovalent residue selected from the group consisting of

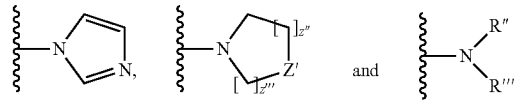

wherein Z' is selected from —CH$_2$—, O, S; z" and z''' are integers independently ranging from 1 to 6, preferably 1 to 3, R" and R''' are monovalent residues each selected independently from the group consisting of hydrogen, alkyl, aryl, aralkyl and —CH$_2$—CH$_2$—(OCH$_2$CH$_2$)$_{y'}$—OH wherein y' is an integer from 1 to 4, preferably methyl, ethyl, hydroxyethyl or —CH$_2$CH$_2$(OCH$_2$CH$_2$)$_{y'}$—OH, wherein y' is an integer from 1 to 4, X' preferably is

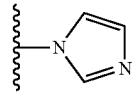 [SMILES: *n1ccnc1]

for the ease of synthesis;
R$^{1'}$ and R$^{2'}$ are divalent residues each selected independently from the group consisting of —(CH$_2$)$_{b'}$—, wherein b' is an integer from 2 to 12, preferably from 2 to 3, and —(CH$_2$)$_{c'}$—[CH(R$^{4'}$)—CH$_2$—O]$_{d'}$—(CH$_2$)$_{e'}$—, wherein c' is an integer ranging from 0 to 3; d' is an integer ranging from 1 to 100, d' preferably ranges from 1 to 20; e' is an integer ranging from 1 to 3; each R$^{4'}$ is independently from each other selected from the group consisting of alkyl, aryl and hydrogen, preferably it is selected from C$_1$- to C$_6$-alkyl, phenyl and hydrogen, more preferably it is selected from hydrogen, methyl, ethyl, propyl, even more preferably it is selected from hydrogen and methyl, most preferably R$^{1'}$ and R$^{2'}$ are selected from 1,2-ethylene (—CH$_2$—CH$_2$—), 1,3-propylene (—CH$_2$—CH$_2$—CH$_2$—), —(CH$_2$)$_2$—O—(CH$_2$)$_2$— and —(CH$_2$)$_2$—O—(CH$_2$)$_2$—O—(CH$_2$)$_2$— group;
R$^{3'}$ is a divalent residue which is selected from the group consisting of alkylene, arylen and —(CH$_2$)$_{f'}$—[CH(R$^{5'}$)—CH$_2$—O]$_{g'}$—(CH$_2$)$_{h'}$—, wherein f' is an integer ranging from 0 to 3; g' is an integer ranging from 1 to 100, g' preferably ranges from 1 to 20; h' is an integer ranging from 1 to 3; each $R^{5'}$ is independently from each other selected from the group consisting of alkyl, aryl and hydrogen, preferably it is selected from $C_1$- to $C_6$-alkyl, phenyl and hydrogen, more preferably it is selected from hydrogen, methyl, ethyl, propyl, even more preferably it is selected from hydrogen and methyl, most preferably $R^{3'}$ is selected from 1,2-ethylene (—$CH_2$—$CH_2$—), 1,3-propylene (—$CH_2$—$CH_2$—$CH_2$—), —$(CH_2)_2$—O—$(CH_2)_2$—, —$(CH_2)_2$—O—$(CH_2)_2$—O—$(CH_2)_2$— and —$(CH_2)_2$—O—$(CH_2)_2$—O—$(CH_2)_2$—O—$(CH_2)_2$— group.

In a preferred embodiment of the present invention and for the ease of synthesis of such compounds, $R^{1'}$ and $R^{2'}$ are selected to be the same and X' is

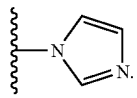

In one embodiment of the present invention $R^{1'}$, $R^{2'}$ and $R^{3'}$ are free of nitrogen atoms as this reduces the undesired formation of side-products during the synthesis of the monomer urea compound of formulae (A1') and (A2'). Nitrogen moieties bound in or to one of said residues might also react with urea forming undesired side-products which then have to be removed by arduous purification methods. The monomer urea compound of formulae (A1') and (A2') are the constituents of the inventive imidazoyl urea polymer forming the respective urea compounds according formulae (A1) and (A2) therein.

The monomer urea compound of the following formulae (A1') and (A2') can be exemplarily prepared using the analogous method disclosed in U.S. Pat. No. 4,157,388, column 3, lines 44 to 66 and example 1. The method converts urea and amines by heating the two components whereby ammonia is set free. Upon using e.g. components having an amino moiety and an imidazoyl moiety bridged by $R^{1'}$ or $R^{2'}$ as respective amines and urea or a diurea bridged by $R^{3'}$ (such as $NH_2$—C(O)—NH—$R^{3'}$—NH—C(O)—$NH_2$) the method can be used to synthesize the inventive monomer urea compounds according to formulae (A1') and (A2') (see exemplarily the preparation of 1,3-Bis-(3-(1H-imidazol-1-yl)propyl)-urea).

The preparation of the imidazoyl urea polymers according to the invention can preferably be carried out in one or more protic and polar solvent. Suitable solvents are water, glycols and alcohols or mixtures thereof, water being preferred. The reaction is preferably carried out at a temperature ranging from 50 to 100° C., more preferably in a temperature interval of 60 and 90° C. The reaction is preferably run until the starting materials are completely consumed or alternatively and preferably for 6 to 160 hours, more preferably for 12 to 140 hours.

In a preferred embodiment of the invention, the molar ratio $$\frac{n_A}{n_B}$$

of the amount of substance $n_A$ of urea compound A (which means in this connection the overall amount of substance of all urea compounds A if more than one is used) to the amount of substance $n_B$ of monomer B (which means in this connection the overall amount of substance of all monomers B if more than one is used) which is employed for the preparation of the imidazoyl urea polymer (s) ranges from 1:1 to 1.5:1, more preferably it ranges from 1.04:1 to 1.4:1, even more preferably, it ranges from 1.05:1 to 1.25:1. It was found by the inventors that if the molar ratio is too high, higher amounts of the inventive imidazoyl urea polymers may be required to allow for sufficiently low dimples to be formed in copper filling of blind microvias (see Applications examples 1 to 7).

The inventive imidazoyl urea polymers can be purified if necessary by any means known to those skilled in the art. These methods include precipitation (of products or of undesired impurities), chromatography, distillation, extraction, flotation or a combination of any of the aforementioned. The purification method to be used depends on the physical properties of the respective compounds present in the reaction mixture and has to be chosen for each individual case. In a preferred embodiment of the present invention, the purification comprises at least one of the following methods selected from the group consisting of extraction, chromatographic and precipitation. Alternatively, the inventive imidazoyl urea polymers can be used without further purification. The same applies mutatis mutandis to monomer urea compounds of formulae (A1') and (A2').

In another embodiment of the present invention, halide ions serving as the counter-ions of the positively charged imidazoyl urea polymers according to the invention are replaced after preparation of the polymer by anions such as methane sulphonate, hydroxide, sulphate, hydrogensulphate, carbonate, hydrogencarbonate, alkylsulphonate such as methane sulphonate, alkarylsulphonate, arylsulphonate, alkylcarboxylate, al karylcarboxylate, arylcarboxylate, phosphate, hydrogenphosphate, dihydrogenphosphate, and phosphonate. The halide ions can be for example replaced by ion-exchange over a suitable ion-exchange resin. The most suitable ion-exchange resins are basic ion-exchange resins such as Amberlyst® A21. Halide ions can then be replaced by adding an inorganic acid and/or an organic acid containing the desired anions to the ion exchange resin. The enrichment of halide ions in an aqueous copper plating bath during use can be avoided if the imidazoyl urea polymers contain anions other than halide ions.

If any (terminal) tertiary amino groups may be present in the imidazoyl urea polymers, they may be converted into the respective quaternary group in accordance with the desired properties by using an organic monohalide or organic monopseudohalides such as benzyl chloride, alkyl chloride, such as 1-chlorohexane or allyl chloride or their corresponding bromides and mesylates, or by using an appropriate mineral acid, such as hydrochloric acid, hydrobromic acid, hydroiodic acid or sulphuric acid.

The imidazoyl urea polymer according to the invention preferably contains one or two polymer terminating groups (PTG1 and/PTG2) that are then bound to a unit derived from urea compound A represented by formula (A1) and/or (A2) and/or divalent residue D in the polymeric building block according to formula (I).

The imidazoyl urea polymers are then represented by the following formulae (IIa) to (IIc)

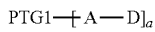 (IIa)

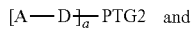 (IIb)

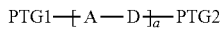 (IIc)

The first polymer terminating group (PTG1) bound to a unit derived from urea compound A in the polymeric building block according to formula (I) can be selected from the group consisting of

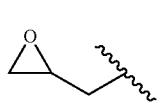 and 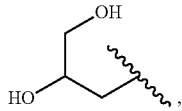, wherein $G^1$, $G^2$, $R^9$ and E are selected from above-defined groups.

The second polymer terminating group (PTG2) bound to divalent residue D in the polymeric building block according to formula (I) can be selected from the group consisting of hydroxyl group (—OH), urea compound A according to formula (A1) or (A2), monovalent residue E, $C_1$- to $C_8$-alkyl, aralkyl, aryl,

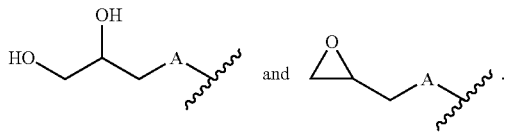

E is selected from above-defined group.

In a preferred embodiment of the present invention, the imidazoyl urea polymer is one according to formula (IIb) and contains a second polymer terminating group (PTG2) which is a urea compound A according to formula (A1) or (A2) and the imidazoyl urea polymer does not contain a first polymer terminating group thereby having only urea compounds A as polymer terminating groups of the polymer.

The imidazoyl urea polymers most preferably can be represented by formula (III)

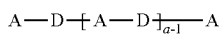 (III)

wherein the polymer terminating groups are both urea compounds according to formulae (A1) or (A2).

The imidazoyl urea polymers preferably have a weight average molecular mass $M_w$ of 1000 to 50000 Da, more preferably of 1500 to 6000 Da, even more preferably of 3000 to 5500 Da. Without being bound by theory, it appears that inventive imidazoyl urea polymers having a weight average molecular mass $M_w$ of 3000 or higher result in less dimple formation when using them as additives for electrolytic copper deposition into recessed structures (see Application Example 1 and 3).

The imidazoyl urea polymers preferably do not contain any organically bound halogen, such as a covalent C—Cl moiety.

In so far as the term "alkyl" is used in this description and in the claims, it refers to a hydrocarbon radical with the general chemical formula $C_wH_{2w+1}$, w being an integer from 1 to about 50. Alkyl residues according to the present invention can be linear and/or branched. In one embodiment, the alkyl residues are unsaturated comprising double or triple bonds between adjacent carbon atoms forming the alkyl residues. If the alkyl residues are unsaturated the corresponding general chemical formula has to be adjusted accordingly. $C_1$-$C_8$-alkyl for example includes, among others, methyl, ethyl, n-propyl, iso-propyl, n-butyl, iso-butyl, tert-butyl, n-pentyl, iso-pentyl, sec-pentyl, tert-pentyl, neo-pentyl, hexyl, heptyl and octyl. Alkyl can be substituted by replacing an H-atom in each case by a functional group, for example hydroxy, halides such as fluorine, chlorine, bromine, iodine, carbonyl, carboxyl, carboxylic acid esters and so forth.

In so far as the term "alkylene" is used in this description and in the claims, it refers to a hydrocarbon diradical with the general chemical formula $C_vH_{2v}$, v being an integer from 1 to about 50. Alkylene residues according to the present invention can be linear and/or branched. In one embodiment, the alkylene residue are unsaturated comprising double or triple bonds between adjacent carbon atoms forming the alkyl residues. If the alkylene residues are unsaturated the corresponding general chemical formula has to be adjusted accordingly. $C_1$-$C_4$-alkylene for example includes, among others, methane-1,1-diyl, ethane-1,2-diyl (also referred in the art and herein as ethylene or 1,2-ethylene), ethane-1,1-diyl, propane-1,3-diyl (also referred in the art and herein as propylene or 1,3-propylene), propane-1,2-diyl, propane-1,1-diyl, butane-1,4-diyl, butane-1,3-diyl, butane-1,2-diyl, butane-1,1-diyl, butane-2,3-diyl. Alkylene can be substituted by replacing an H-atom in each case by a functional group, for example hydroxy, halides such as fluorine, chlorine, bromine, iodine, carbonyl, carboxyl, carboxylic acid esters and so forth.

In so far as the term "aryl" is used in this description and in the claims, it refers to ring-shaped aromatic hydrocarbon radical, for example phenyl or naphtyl, where individual ring carbon atoms can be replaced by N, O and/or S, for example benzothiazolyl. Furthermore, aryl can be substituted by replacing an H-atom in each case by a functional group, for example hydroxy, halides such as fluorine, chlorine, bromine, iodine, carbonyl, carboxyl, carboxylic acid esters and so forth. In analogy to alkyl and alkylene, arylen is to be understood as ring-shaped aromatic hydrocarbon diradical with the same provisions as stated for aryl.

In so far as the term "aralkyl" is used in this description and in the claims, it refers to a hydrocarbon radical consisting of an alkyl and an aryl radical such as benzyl and tolyl.

The terms "polymeric" and "polymer" have to be understood in a broad sense in connection with the present invention. They comprise any compound which has been formed by reaction of at least one monomer urea compound of formulae (A1') and/or (A2') and at least one monomer B. The term "polymer" does comprise compounds which are typically designated as oligomers. The bonding sites in some chemical formulae are emphasised by a wavy line ("〜〜") as is customary in the art.

The inventive metal or metal alloy plating bath comprising at least one source of metal ions is characterised in that it further comprises at least one imidazoyl urea polymer. If only one source of reducible metal ions is present in the plating bath according to the invention only this metal will be deposited when using the metal plating bath. If two or more sources of reducible metal ions are present therein an alloy will be deposited. Preferably, the at least one source of metal ions is a source of copper ions. More preferably, 99 weight percent or more of the reducible metal ions are copper ions.

More preferably, the aqueous copper plating bath according to the invention comprises a source of copper ions and an acid and is characterised in that it comprises at least one imidazoyl urea polymer.

The concentration of the at least one imidazoyl urea polymer in the aqueous metal or metal alloy plating bath, preferably aqueous copper plating bath, advantageously ranges from 0.1 mg/L to 1000 mg/L, more advantageously from 0.5 mg/L to 500 mg/L and most advantageously from 1 mg/L to 400 mg/L.

The aqueous metal or metal alloy plating bath according to the invention is an aqueous solution. The term "aqueous solution" means that the prevailing liquid medium, which is the solvent in the solution, is water. Further liquids, that are miscible with water, as for example alcohols and other polar organic liquids may be added.

The aqueous metal or metal alloy plating bath according to the invention may be prepared by dissolving all components in aqueous liquid medium, preferably in water.

The aqueous metal or metal alloy plating bath contains a source of metal ions which can be any water soluble metal salt. The preferred aqueous copper plating bath contains at least one source of copper ions which is preferably selected from the group consisting of copper sulphate and copper alkyl sulphonates such as copper methane sulphonate. Further copper ion sources can be copper oxide and copper carbonate. The copper ion concentration in the aqueous copper plating bath preferably ranges from 10 g/L to 70 g/L.

The preferred aqueous copper plating bath further contains at least one acid which is preferably selected from the group consisting of sulphuric acid, fluoroboric acid, phosphoric acid and methane sulphonic acid and is preferably added in a concentration of 10 g/L to 400 g/L, more preferably from 20 g/L to 250 g/L.

The preferred aqueous copper plating bath composition preferably has a pH value of ≤2, more preferably of ≤1.

The preferred aqueous copper plating bath preferably further contains at least one accelerator-brightener additive which is selected from the group consisting of organic thiol-, sulphide-, disulphide- and polysulphide-compounds. Preferred accelerator-brightener additives are selected from the group consisting of 3-(benzthiazolyl-2-thio)-propylsulphonic-acid, 3-mercaptopropan-1-sulphonic acid, ethylendithiodipropylsulphonic-acid, bis-(p-sulphophenyl)-disulphide, bis-(ω-sulpho-butyl)-disulphide, bis-(ω-sulphohydroxypropyl)-disulphide, bis-(ω-sulphopropyl)-disulphide, bis-(ω-sulphopropyl)-sulphide, methyl-(ω-sulphopropyl)-disulphide, methyl-(ω-sulfopropyl)-trisulphide, O-ethyl-dithiocarbonic-acid-S-(ω-sulphopropyl)-ester, thioglycol-acid, thiophosphoric-acid-O-ethyl-bis-(ω-sulphopropyl)-ester, 3-N, N-dimethylaminodithiocarbamoyl-1-propanesulphonic acid, 3,3'-thiobis(1-propanesulphonic acid), thiophosphoric-acid-tris-(ω-sulphopropyl)-ester and their corresponding salts. The concentration of all accelerator-brightener additives optionally present in the aqueous acidic copper bath compositions preferably ranges from 0.01 mg/L to 100 mg/L, more preferably from 0.05 mg/L to 50 mg/L.

The preferred aqueous copper plating bath optionally contains in addition to the imidazoyl urea polymer at least one further carrier-suppressor additive which is preferably selected from the group consisting of polyvinylalcohol, carboxymethylcellulose, polyethylenglycol, polypropylenglycol, stearic acid polyglycolester, alkoxylated naphtoles, oleic acid polyglycolester, stearylalcoholpo-lyglycolether, nonylphenolpolyglycolether, octanolpolyalkyleneglycolether, octanediol-bis-(polyalkyleneglycolether), poly(ethylenglycol-ran-propylenglycol), poly(ethylengly-col)-block-poly(propylenglycol)-block-poly(ethylenglycol), and poly(propylenglycol)-block-poly(ethylenglycol)-block-poly(propylenglycol). More preferably, the optional carrier-suppressor additive is selected from the group consisting of polyethylenglycol, polypropylenglycol, poly(ethylenglycol-ran-propylenglycol), poly(ethylenglycol)-block-poly(propyleneglycol)-block-poly(ethylenglycol) and poly(propyleneglycol)-block-poly(ethylenglycol)-block-poly(propyleneglycol). The concentration of said optional carrier-suppressor additive preferably ranges from 0.005 g/L to 20 g/L, more preferably from 0.01 g/L to 5 g/L.

Optionally, the preferred aqueous copper plating bath contains in addition to the inventive imidazoyl urea polymer at least one further leveller additive selected from the group consisting of nitrogen containing organic compounds such as polyethyleneimine, alkoxylated polyethyleneimine, alkoxylated lactames and polymers thereof, diethylenetriamine and hexamethylenetetramine, polyethylenimine bearing peptides, polyethylenimine bearing amino acids, polyvinylalcohol bearing peptides, polyvinylalcohol bearing amino acids, polyalkyleneglycol bearing peptides, polyalkyleneglycol bearing amino acids, aminoalkylene bearing pyrrols and aminoalkylene bearing pyridines, organic dyes such as Janus Green B, Bismarck Brown Y and Acid Violet 7, sulphur containing amino acids such as cysteine, phenazinium salts and derivatives thereof. Suitable ureyl polymers have been disclosed in EP 2735627 A1, said polyalkyleneglycol bearing amino acids and peptides are published in EP 2113587 B9 and EP 2537962 A1 teaches suitable aminoalkylene bearing pyrrols and pyridines. The preferred further leveller additive is selected from nitrogen containing organic compounds. Said optional leveller additive is added to the aqueous copper plating bath in amounts of 0.1 mg/L to 100 mg/L.

The preferred aqueous copper plating bath optionally further contains at least one source of halide ions, preferably chloride ions in a quantity of 20 mg/L to 200 mg/L, more preferably from 30 mg/L to 60 mg/L. Suitable sources for halide ions are for example hydrochloric acid or alkali halides such as sodium chloride.

Optionally, the preferred aqueous copper plating bath may contain at least one wetting agent. These wetting agents are also referred to as surfactants in the art. The at least one wetting agent may be selected from the group of non-ionic, cationic and/or anionic surfactants and is used in concentration from 0.01 to 5 wt.-%.

In one embodiment of the present invention, a redox couple, such as $Fe^{2+/3+}$ ions is added to the preferred aqueous copper plating bath. Such a redox couple is particularly useful, if reverse pulse plating is used in combination with inert anodes for copper deposition. Suitable processes for copper plating using a redox couple in combination with reverse pulse plating and inert anodes are for example disclosed in U.S. Pat. Nos. 5,976,341 and 6,099,711. The preferred aqueous copper plating bath is particularly suitable for electrolytic deposition of copper.

A method for deposition of a metal or metal alloy, preferably copper or copper alloy, onto a substrate comprising, in this order, the steps
(i) providing a substrate,
(ii) contacting the substrate with an aqueous metal or metal alloy plating bath according to the invention, and
(iii) applying an electrical current between the substrate and at least one anode,
and thereby depositing a metal or metal alloy, preferably copper or copper alloy, on at least a portion of the surface of a substrate.

More preferably, pure copper (i.e. in the context of the present invention copper of 98 wt.-%, even more preferably of 99 wt.-%) is deposited.

The substrate is preferably selected from the group consisting of printed circuit boards, IC substrates, circuit carriers, interconnect devices, semiconducting wafers and glass substrates. Preferred are substrates of the afore-mentioned group which have recessed structures such as trenches, blind micro vias, through silicon vias and through glass vias. Metal or metal alloy, preferably copper or copper alloys, are then deposited into these recessed structures.

The metal or metal alloy plating bath according to the invention is operated from 10 to 100° C. for any time sufficient to deposit the desired deposit thickness. The preferred aqueous copper plating bath is preferably operated in the method according to the present invention in a temperature range of 15° C. to 50° C., more preferably in a temperature range of 20° C. to 40° C. by applying an electrical current to the substrate and at least one anode. Preferably, a cathodic current density range of 0.05 A/dm$^2$ to 12 A/dm$^2$, more preferably 0.1 A/dm$^2$ to 7 A/dm$^2$ is applied.

The aqueous metal or metal alloy plating bath plating bath according to the present invention can be used for DC plating and reverse pulse plating. Both inert and soluble anodes can be utilised when depositing metal or metal alloy such as copper from the plating bath according to the present invention.

The aqueous metal or metal alloy plating bath can be either used in conventional vertical or horizontal plating equipment. The substrate or at least a portion of its surface may be contacted with the aqueous metal or metal alloy plating bath according to the invention by means of spraying, wiping, dipping, immersing or by other suitable means. Thereby, a metal or metal alloy, preferably copper or copper alloy, layer is obtained on at least a portion of the surface of the substrate.

It is preferential to agitate the aqueous metal or metal alloy plating bath during the plating process, i.e. the deposition of metal or metal alloy. Agitation may be accomplished for example by mechanical movement of the inventive aqueous copper plating bath like shaking, stirring or continuously pumping of the liquids or by ultrasonic treatment, elevated temperatures or gas feeds (such as purging the electroless plating bath with air or an inert gas such as argon or nitrogen).

The process according to the invention may comprise further cleaning, (micro-) etching, reducing, rinsing and/or drying steps all of which are known in the art.

It is an advantage of the present invention that the inventive imidazoyl urea polymer may be used in the aqueous metal or metal alloy plating bath, preferably in the copper plating bath, without further leveller and/or carrier-suppressor as the inventive imidazoyl urea polymer is dual-functional and acts as leveller and/or carrier-suppressor (use of Preparation Examples 6 and 7 in Applications Examples 20 to 27).

It is another advantage of the present invention that the aqueous copper plating bath allows for uniformal filling of recessed structures and that the deposits are free of voids and dimples. Uniformal filling is to be understood in the context of the present invention that different recessed structures having different aspect ratios such as trenches which generally have an aspect ratio of <1 and vias generally which have an aspect ratio of >1 can be filled in one step resulting in similar layer distribution in these different recessed structures having different aspect ratios.

The invention will now be illustrated by reference to the following non-limiting examples.

EXAMPLES $^1$H-NMR spectra were recorded at 250 MHz with a spectrum offset of 4300 Hz, a sweep width of 9542 Hz at 25° C. (Varian, NMR System 250). The solvent used was d$^6$-DMSO unless stated otherwise.

The weight average molecular mass M$_w$ of the imidazoyl urea polymers was determined by gel permeation chromatography (GPC) using a GPC apparatus from WGE-Dr. Bures equipped with a molecular weight analyzer BI-MwA from Brookhaven, a TSK Oligo +3000 column, and Pullulan and PEG standards with M$_w$=400 to 22000 g/mol. The solvent used was Millipore water with 0.5% acetic acid and 0.1 M Na$_2$SO$_4$. Conc. is used herein as abbreviation for concentration.

Preparation of 1,3-Bis-(3-(1H-imidazol-1-yl)propyl)-urea (Synthesis of an Inventive Monomer)

A 500 mL round bottom flask was charged with 44.1 g (727 mmol) urea and 186 g (1454 mmol) 3-(1H-Imidazol-1-yl)propan-1-amine (CAS-No. 5036-48-6). The reaction mixture was heated to 150° C. within 20 minutes. Upon reaching a temperature of about 145° C. a moderate ammonia formation was observed. The reaction mixture was kept at 150° C. overnight. After completion of the reaction, any residual ammonia was removed under reduced pressure (10 mbar) at 50° C. 200 g (99.5% yield) of a clear, pale brown and viscous liquid were obtained.

$^1$H-NMR (d$_6$-DMSO, 250 MHz): δ 7.82 (s; 2H); 7.17 (s; 2H); 6.88 (s; 2H); 5.97 (s; 2H); 3.94 (t; $^3J_{HH}$=7.5 Hz; 4H); 2.96 (dd; $^3J_{HH}$=7.5 Hz; $^4J_{HH}$=7.5 Hz; 4H); 1.79 (t; $^3J_{HH}$=7.5 Hz; 4H)

Preparation Example 1

In a 100 mL glass reactor equipped with reflux condenser 14.41 g (52.1 mmol) 1,3-Bis-(3-(1H-imidazol-1-yl)propyl)-urea were dissolved in 30 mL water and heated to 80° C. Then, 5.65 g (39.1 mmol) dichlorodiethylether (CAS-No. 111-44-4) was added drop-wise within 5 min and the reaction mixture was stirred for further 30 h at 80° C. 50 g of a clear orange solution containing the imidazoyl urea polymer (40 wt.-% in water) were obtained (M$_w$=2840 Da).

Preparation Example 2

In a 100 mL glass reactor equipped with reflux condenser 13.57 g (49.1 mmol) 1,3-Bis-(3-(1H-imidazol-1-yl)propyl)-urea were dissolved in 30 mL water and heated to 80° C. Then, 6.50 g (45.0 mmol) dichlorodiethylether was added drop-wise within 5 min and the reaction mixture was stirred for further 30 h at 80° C. 50 g of a clear orange solution containing the imidazoyl urea polymer (40 wt.-% in water) were obtained ($M_w$=4879 Da).

Preparation Example 3

In a 100 mL glass reactor equipped with reflux condenser 12.34 g (44.7 mmol) 1,3-Bis-(3-(1H-imidazol-1-yl)propyl)-urea were dissolved in 30 mL water and heated to 80° C. Then, 7.81 g (40.9 mmol) 1,2-Bis(2-chloroethoxy)ethane was added drop-wise within 5 min and the reaction mixture was stirred for further 30 h at 80° C. 50 g of a clear orange solution containing the imidazoyl urea polymer (40 wt.-% in water) were obtained ($M_w$=3437 Da).

Preparation Example 4

In a 100 mL glass reactor equipped with reflux condenser 10.29 g (37.2 mmol) 1,3-Bis-(3-(1H-imidazol-1-yl)propyl)-urea were dissolved in 25.11 mL water and heated to 80° C. Then, 6.65 g (27.9 mmol) 1-Chloro-2-(2-(2-(2-(2-chloroethoxy)ethoxy)ethoxy)ethane (CAS-No. 638-56-2) was added drop-wise within 5 min and the reaction mixture was stirred for further 51 h at 80° C. 41.85 g of a clear orange solution containing the imidazoyl urea polymer (40 wt.-% in water) were obtained ($M_w$=3447 Da).

Preparation Example 5

In a 100 mL glass reactor equipped with reflux condenser 11.32 g (41.0 mmol) 1,3-Bis-(3-(1H-imidazol-1-yl)propyl)-urea were dissolved in 30 mL water and heated to 80° C. Then, 8.94 g (37.5 mmol) 1-Chloro-2-(2-(2-(2-(2-chloroethoxy)ethoxy)ethoxy)ethane was added drop-wise within 5 min and the reaction mixture was stirred for further 51 h at 80° C. 41.85 g of a clear orange solution containing the imidazoyl urea polymer (40 wt.-% in water) were obtained ($M_w$=4316 Da).

Preparation Example 6

In a 100 mL glass reactor equipped with reflux condenser 13.37 g (48.4 mmol) 1,3-Bis-(3-(1H-imidazol-1-yl)propyl)-urea were dissolved in 45 mL water and heated to 80° C. Then, 16.64 g (36.3 mmol) Ethan-1,2-diyl-bis(oxy)bis(ethan-2,1-diyl)bis(4-methylbenzensulphonat) was added drop-wise within 5 min and the reaction mixture was stirred for further 18.5 h at 80° C. 75 g of a clear yellow solution containing the imidazoyl urea polymer (40 wt.-% in water) were obtained ($M_w$=3400 Da).

Preparation Example 7

In a 100 mL glass reactor equipped with reflux condenser 19.77 g (71.5 mmol) 1,3-Bis-(3-(1H-imidazol-1-yl)propyl)-urea were dissolved in 45 mL water and heated to 80° C. Then, 10.33 g (71.5 mmol) dichlorodiethylether was added drop-wise within 5 min and the reaction mixture was stirred for further 74.5 h at 80° C. 75 g of a clear yellow solution containing the imidazoyl urea polymer (40 wt.-% in water) were obtained ($M_w$=3900 Da).

Preparation Example 8: Regioselectivity of Nucleophilic Attack on 1,3-Bis-(3-(1H-imidazol-1-yl)propyl)-urea In a 100 mL glass reactor 5 g (18.1 mmol) 1,3-Bis-(3-(1H-imidazol-1-yl)propyl)-urea was dissolved in 40.76 mL water and heated to 50° C. Then, 5.19 g (36.2 mmol) methyliodide were added drop-wise to the solution and the reaction mixture was stirred for 22 h. A product mixture containing four compounds was obtained wherein the individual compounds were analysed by NMR using the integers and chemical shifts of the individual compounds:

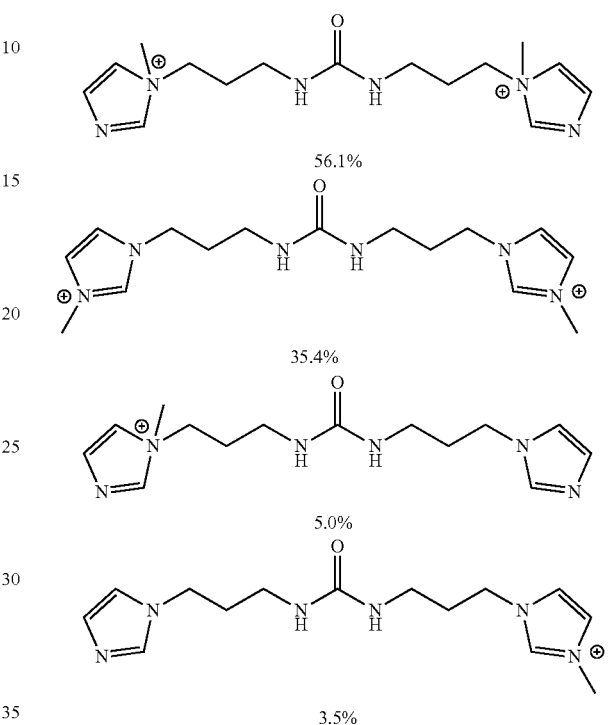

This reaction served as a model reaction to assess the regioselectivity during the polymerisation. A slight selectivity of the addition of the alkyl groups to the nitrogen atoms bearing the alkaline group was found.

Copper Deposition into BMVs':

The electrolyte baths containing the imidazoyl urea polymers prepared according to preparation examples 1 to 5 were used as additives for deposition of copper into recessed structures and then subjected to the following test method.

A sufficient BMV filling with copper means that the copper deposit has no or almost no so-called dimple. An insufficient BMV filling is characterised by a concave structure of the copper deposit, i.e. by a dimple. Hence, the copper surface of a sufficiently filled BMV is as even as possible. Voids in a copper filled via are also not desired. Industrial processes require dimples of 5 μm or less nowadays.

The cross sections of recessed structures filled with copper were investigated with an optical microscope after depositing a protection layer of nickel onto the copper deposit and applying conventional grinding and polishing methods.

The values for the "dimples" were recorded with a chromatic sensor (Nanofocus μ-scan with sensor CRT5).

Methods for Application Examples 1 to 7

Equipment: Gornall cell with 1.8 L volume, bath agitation with a pump, no air injection, soluble copper anodes.

A copper electroplating bath stock solution comprising 50 g/L $Cu^{2+}$ ions (added as copper sulphate), 50 g/L sulphuric acid, 45 mg/L $Cl^-$ ions, 300 mg/L polyethylenglycol as a carrier-suppressor additive and 1.4 mL/L of a solution containing an standard sulphur-organic brightener additive (Cupracid® Brightener, product of Atotech Deutschland GmbH) was used. The imidazoyl urea polymers were added to said stock solution.

A current density of 1.2 $A/dm^2$ was applied throughout all application examples. The thickness of copper plated onto the top surface of the substrate was in average 15 μm. The plating time was 57 min. The test panels were cleaned, microetched and rinsed prior to electroplating of copper.

The test panels used throughout the application examples comprised BMVs' (depth×diameter: 70×40 μm and 100×40 μm). The size of the test panels was 7.5×10 cm. The results are summarised in the following table.

TABLE 1

Application examples (BMV filling capability)

| # | Imidazoyl urea polymers | Imidazoyl urea polymer conc. [mg/L] | Conc. brightener [mL/L] | Dimple [μm] in 70 × 40 μm BMVs' | Dimple [μm] in 100 × 40 μm BMVs' |
|---|---|---|---|---|---|
| 1 | Preparation Example 1 | 10 | 2.0 | <5 μm | 8 μm |
| 2 | Preparation Example 1 | 50 | 1.4 | <5 μm | <5 μm |
| 3 | Preparation Example 2 | 10 | 2.0 | <5 μm | <5 μm |
| 4 | Preparation Example 3 | 10 | 2.0 | <5 μm | <5 μm |
| 5 | Preparation Example 4 | 10 | 2.0 | <5 μm | 10 μm |
| 6 | Preparation Example 4 | 30 | 2.0 | <5 μm | <5 μm |
| 7 | Preparation Example 5 | 10 | 2.0 | <5 μm | <5 μm |

Blind micro vias (BMV) having dimensions of 70×40 μm and 100×40 μm were filled with copper using plating baths containing the inventive imidazoyl urea polymers. The dimples of the 70×40 μm BMVs' were all sufficiently low to satisfy today's industrial requirements, i.e. they were below 5 μm. The dimples of the 100×40 μm BMVs' were mostly sufficiently low but in the cases of imidazoyl urea polymers according to preparations examples 1 and 4 higher concentrations of the additives were necessary in order to allow for dimples of 5 μm or smaller to be formed. Without being bound by theory, this may be caused by the higher molar ratio of monomer A to B of 1.33.

Application Examples 8 to 19

The copper electroplating bath stock solution of Application Examples 1 to 7 was used and imidazoyl urea polymers were added in varying concentrations (see Table 2). The method described above was used and BMV's were filled with copper. The results are summarised in the following table.

TABLE 2

Application examples (BMV filling capability)

| # | Imidazoyl urea polymers | Imidazoyl urea polymer conc. [mg/L] | Conc. brightener [mL/L] | Dimple [μm] in 70 × 40 μm BMVs' | Dimple [μm] in 100 × 40 μm BMVs' |
|---|---|---|---|---|---|
| 8 | Preparation Example 2 | 1 | 1.4 | <5 μm | 15-20 μm |
| 9 | Preparation Example 2 | 3 | 1.4 | <5 μm | <5 μm |
| 10 | Preparation Example 2 | 5 | 1.4 | <5 μm | <5 μm |
| 11 | Preparation Example 2 | 10 | 1.4 | <5 μm | <5 μm |
| 12 | Preparation Example 2 | 30 | 1.4 | <5 μm | <5 μm |
| 13 | Preparation Example 2 | 50 | 1.4 | <5 μm | <5 μm |
| 14 | Preparation Example 3 | 1 | 1.4 | 10-15 μm | 15-20 μm |
| 15 | Preparation Example 3 | 3 | 1.6 | <5 μm | <5 μm |
| 16 | Preparation Example 3 | 5 | 1.8 | <5 μm | <5 μm |
| 17 | Preparation Example 3 | 10 | 2.0 | <5 μm | <5 μm |
| 18 | Preparation Example 3 | 30 | 2.2 | <5 μm | <5 μm |
| 19 | Preparation Example 3 | 50 | 2.4 | <5 μm | <5 μm |

The values observed for dimples in both 70×40 μm and 100×40 μm BMVs' complied with industrial requirements with very few exceptions, i.e. they were below 5 μm. The inventive imidazoyl urea polymers of preparation example 2 as additive in the plating bath allowed for dimples of less than 5 μm to be formed when filling 70×40 μm BMV in a concentration of 1 mg/L already. The bigger BMVs required 3 mg/L of said polymer as additive. The latter concentration was also necessary in case of inventive imidazoyl urea polymers of preparation example 3 as additive for both tested BMVs in order to provide copper fillings without too big dimples. The difference in performance of the two polymers—although not entirely understood—might be associated with the difference in average molecular mass $M_w$.

Methods for Application Examples 20 to 27
(without Carrier-Suppressor)

A copper electroplating bath stock solution comprising 50 g/L $Cu^{2+}$ ions (added as copper sulphate), 50 g/L sulphuric acid, 45 mg/L $Cl^-$ ions and varying amounts of a solution containing an organic brightener additive (Cupracid® Brightener, product of Atotech Deutschland GmbH) as given in Table 3 were used. The imidazoyl urea polymers were added to said stock solution.

The copper electroplating bath was used for BMV filling with copper as described for Applications Examples 1 to 7. The results are summarised in the following table.

TABLE 3

Application examples (BMV filling capability)

| # | Imidazoyl urea polymers | Imidazoyl urea polymer conc. [mg/L] | Conc. brightener [mL/L] | Dimple [μm] in 70 × 40 μm BMVs' | Dimple [μm] in 100 × 40 μm BMVs' |
|---|---|---|---|---|---|
| 20 | Preparation Example 7 | 5 | 1.8 | 5 μm | 11 μm |
| 21 | Preparation Example 7 | 30 | 2.2 | 0 μm | 4 μm |
| 22 | Preparation Example 7 | 50 | 2.4 | 0 μm | 3 μm |
| 23 | Preparation Example 8 | 50 | 1.4 | <5 μm | — |
| 24 | Preparation Example 8 | 100 | 1.6 | <5 μm | — |
| 25 | Preparation Example 8 | 200 | 1.8 | <5 μm | — |
| 26 | Preparation Example 8 | 300 | 2.0 | <5 μm | — |
| 27 | Preparation Example 8 | 400 | 2.2 | <5 μm | — |

The values observed for dimples in both 70×40 μm and 100×40 μm BMVs' complied with industrial requirements, i.e. they were below 5 μm. In several cases no dimples were formed at all and evenly formed copper deposits were obtained. Since no additional carrier-suppressor was added a higher concentration of the inventive imidazoyl urea polymers was required. 30 mg/L of the inventive imidazoyl urea polymer of preparation example 6 was sufficient for small enough dimples of the copper deposition to satisfy today's production requirements and no additional carrier-suppressor or leveller was needed. Since no carrier-suppressor is necessary, the overall concentration of additives in the plating bath can be reduced resulting in cost savings and less chemistry consumption which is advantageous for ecological reasons.

Other embodiments of the present invention will be apparent to those skilled in the art from a consideration of this specification or practice of the invention disclosed herein. It is intended that the specification and examples be considered as exemplary only, with the true scope of the invention being defined by the following claims only.

The invention claimed is:

1. An imidazoyl urea polymer comprising a polymeric building block according to formula (I)

(I)

wherein A represents a unit of one or both of the following formulae (A1) and (A2)

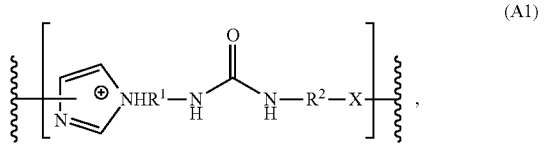
(A1)

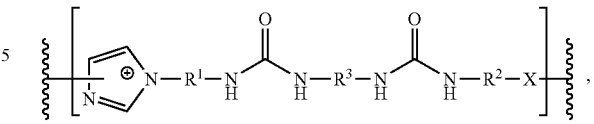
(A2)

wherein
X is a divalent residue selected from the group consisting of

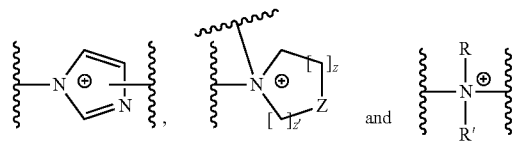

wherein Z is selected from —CH$_2$—, O, S; z and z' are integers independently ranging from 1 to 6, R and R' are monovalent residues each selected independently from the group consisting of hydrogen, alkyl, aryl, aralkyl and —CH$_2$—CH$_2$—(OCH$_2$CH$_2$)$_y$—OH wherein y is an integer from 1 to 4;

R$^1$ and R$^2$ are divalent residues each selected independently from the group consisting of —(CH$_2$)$_b$— and —(CH$_2$)$_b$—[CH(R$^4$)—CH$_2$O]$_d$—(CH$_2$)$_e$— wherein b is an integer ranging from 2 to 12; wherein c is an integer ranging from 0 to 3; d is an integer ranging from 1 to 100; e is an integer ranging from 1 to 3; each R$^4$ is independently from each other selected from the group consisting of alkyl, aryl and hydrogen;

R$^3$ is a divalent residue which is selected from the group consisting of alkylene, arylene and —(CH$_2$)$_f$[CH(R$^5$)—CH$_2$—O]$_g$—(CH$_2$)$_h$—, wherein f is an integer ranging from 0 to 3; g is an integer ranging from 1 to 100; h is an integer ranging from 1 to 3; each R$^5$ is independently from each other selected from the group consisting of alkyl, aryl and hydrogen;

a is an integer and ranges from 1 to 40; and

D is a divalent residue and is selected from the group consisting of —CH$_2$—CH(OH)—CH$_2$—, —CH$_2$—CH(SH)—CH$_2$—, —(CH$_2$)$_i$—[CH(R$^6$)—CH$_2$—O]$_j$—(CH$_2$)$_k$— and —CH$_2$—CH(OH)—(CH$_2$)$_l$—[CH(R$^7$)—CH$_2$—O]$_m$—(CH$_2$)$_n$—CH(OH)—CH$_2$— wherein i is an integer ranging from 0 to 3; j is an integer ranging from 1 to 100; k is an integer ranging from 1 to 3; each R$^6$ is independently from each other selected from the group consisting of alkyl, aryl and hydrogen; l is an integer ranging from 1 to 3; m is an integer ranging from 1 to 100; n is an integer ranging from 1 to 3; each R$^7$ is independently from each other selected from the group consisting of alkyl, aryl and hydrogen;

wherein the individual units A may be the same or different, and wherein the individual units D may be the same or different.

2. The imidazoyl urea polymer according to claim 1 wherein R$^1$ and R$^2$ are selected from 1,2-ethylene (—CH$_2$—CH$_2$—), 1,3-propylene (—CH$_2$—CH$_2$—CH$_2$—), —(CH$_2$)$_2$—O—(CH$_2$)$_2$— and —(CH$_2$)$_2$—O—(CH$_2$)$_2$—O—(CH$_2$)$_2$— group and R$^3$ is selected from 1,2-ethylene —CH$_2$—CH$_2$—), 1,3-propylene (—CH$_2$—CH$_2$—CH$_2$—), —(CH$_2$)$_2$—O—(CH$_2$)$_2$—, —(CH$_2$)$_2$—O—(CH$_2$)$_2$—O—(CH$_2$)$_2$— and —(CH$_2$)$_2$—O—(CH$_2$)$_2$—O—(CH$_2$)$_2$—O—(CH$_2$)$_2$— group.

3. The imidazoyl urea polymer according to claim 2 wherein X is

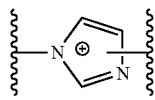

and D is selected from —CH$_2$—CH(OH)—CH$_2$—, —(CH$_2$)$_i$—[CH(R$^6$)—CH$_2$—O]$_j$—(CH$_2$)$_k$—, and —CH$_2$—CH(OH)—(CH$_2$)$_l$—[CH(R$^7$)—CH$_2$—O]$_m$—(CH$_2$)$_n$—CH(OH)—CH$_2$—.

4. The imidazoyl urea polymer according to claim 3 wherein R$^1$, R$^2$ and R$^3$ are free of nitrogen atoms.

5. The imidazoyl urea polymer according to claim 4 wherein A is selected to be one or more units derived from formula (A1).

6. The imidazoyl urea polymer according to claim 1 wherein X is

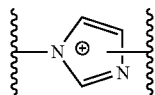

and D is selected from —CH$_2$—CH(OH)—CH$_2$—, —(CH$_2$)$_i$—[CH(R$^6$)—CH$_2$—O]$_j$—(CH$_2$)$_k$— and —CH$_2$—CH(OH)—(CH$_2$)$_l$—[CH(R$^7$)—CH$_2$—O]$_m$—(CH$_2$)$_n$—CH(OH)—CH$_2$—.

7. The imidazoyl urea polymer according to claim 6 wherein D is —(CH$_2$)$_o$—[CH(R$^8$)—CH$_2$—O]$_p$—(CH$_2$)$_q$—, o is 0 and p is an integer ranging from 1 to 100 and q is an integer ranging from 1 to 3.

8. The imidazoyl urea polymer according to claim 1 wherein R$^1$, R$^2$ and R$^3$ are free of nitrogen atoms.

9. The imidazoyl urea polymer according to claim 1 wherein A is selected to be one or more units derived from formula (A1).

10. The imidazoyl urea polymer comprising a polymeric building block according to claim 1 wherein the imidazoyl urea polymers are represented by one of the following formulae (IIa) to (IIc)

PTG1—[A—D]$_a$ (IIa)

[A—D]$_a$—PTG2 and (IIb)

PTG1—[A—D]$_a$—PTG2 (IIc)

wherein the imidazoyl urea polymer contains one or two polymer terminating groups (PTG1) and/or (PTG2) that are bound to the unit A represented by formula (A1) and/or (A2) and/or to the divalent residue D in the polymeric building block according to formula (I) and wherein the first polymer terminating group (PTG1) bound to the unit A in the polymeric building block according to formula (I) is selected from the group consisting of
E-G$^1$-, R$^9$-G$^2$-,

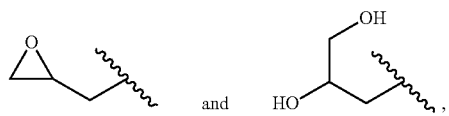 [SMILES: *CC1CO1 ; *CC(O)CO]

and the second polymer terminating group (PTG2) bound to the divalent residue D in the polymeric building block according to formula (I) is selected from the group consisting of hydroxyl group (—OH), urea compound A according to formula (A1) or (A2), monovalent residue E, C$_1$- to Ca-alkyl, aralkyl, aryl,

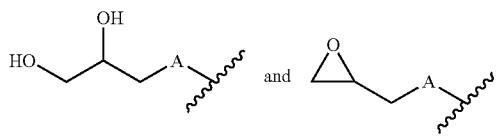

wherein G$^1$ and G$^2$ are divalent residues represented by the following formula —(CH$_2$)$_r$—[CH(R$^{10}$)—CH$_2$—O]$_s$—(CH$_2$)$_t$— wherein r is an integer ranging from 0 to 3; s is an integer ranging from 1 to 100; t is an integer ranging from 1 to 3; each R$^{10}$ is independently from each other selected from the group consisting of alkyl, aryl and hydrogen; E is selected from triflate, nonaflate, alkylsulphonates, arylsulphonates and halogenides; and R$^9$ is a monovalent residue selected from the group consisting of C$_1$- to C$_8$-alkyl, C$_1$- to C$_8$-alkenyl, aralkyl and aryl.

11. The imidazoyl urea polymer according to claim 1 wherein the imidazoyl urea polymers have a weight average molecular mass M$_w$ of 1000 to 50000 Da.

12. A process for forming an imidazoyl urea polymer, comprising reacting a monomer urea compound of the following formulae (A1') and (A2')

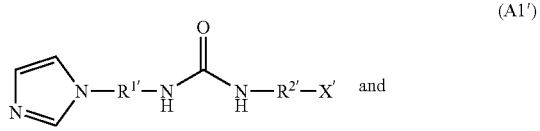

(A1')

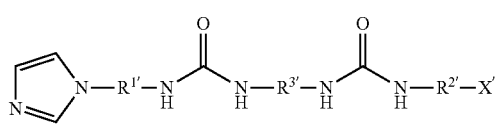

(A2')

wherein

X' is a monovalent residue selected from the group consisting of

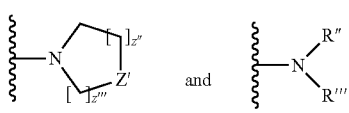

wherein Z' is selected from —CH$_2$—, O, S;
z" and z'" are integers independently ranging from 1 to 6;
R" and R'" are monovalent residues each selected independently from the group consisting of hydrogen, alkyl, aryl, aralkyl and —CH$_2$—CH$_2$—(OCH$_2$CH$_2$)$_{y'}$—OH, wherein y' is an integer from 1 to 4;

R$^{1'}$ and R$^{2'}$ are divalent residues each selected independently from the group consisting of —CH$_2$)$_{b'}$—, wherein b' is an integer from 2 to 12, and —CH$_2$)$_{c'}$—[CH(R$^4$)—CH$_2$—O]$_{d'}$—(CH$_2$)$_{e'}$—, wherein c' is an integer ranging from 0 to 3; d' is an integer ranging from 1 to 100; e' is an integer ranging from 1 to 3; each R$^{4'}$ is independently from each other selected from the group consisting of alkyl, aryl and hydrogen;

R$^{3'}$ is a divalent residue which is selected from the group consisting of alkylene, arylene and —(CH$_2$)$_{f'}$—[CH(R$^9$)—CH$_2$—O]$_{g'}$, —(CH$_2$)$_{h'}$, wherein f' is an integer ranging from 0 to 3; g' is an integer ranging from 1 to 100; h' is an integer ranging from 1 to 3; each R$^{5'}$ is independently from each other selected from the group consisting of alkyl, aryl and hydrogen, with one or more monomers B selected from the group consisting of (B1), (B2), (B3) or (B4), each of which are represented by the following formulae

E-G$^1$-E (B1),

E-G$^2$-R$^9$ (B2),

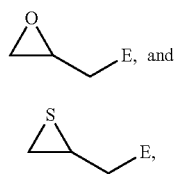

(B3)

(B4)

wherein

G$^1$ and G$^2$ are divalent residues represented by the following formula —(CH$_2$)$_r$—[CH(R$^{10}$)—CH$_2$—O]$_s$—(CH$_2$)$_t$— wherein r is an integer ranging from 0 to 3, s is an integer ranging from 1 to 100, t is an integer ranging from 1 to 3; each R$^{10}$ is independently from each other selected from the group consisting of alkyl, aryl and hydrogen;

E each represents a leaving group individually selected from triflate, nonaflate, alkylsulphonates, arylsulphonates and halogenides; and R$^9$ is a monovalent residue selected from the group consisting of C$_1$- to C$_8$-alkyl, C$_1$- to C$_8$-alkenyl, aralkyl, and aryl, wherein the reacting is carried out in one or more polar protic solvent at a temperature ranging from 50° C. to 100° C. until the one or more monomers B is completely consumed.

13. The process according to claim 12, wherein the reacting is carried out for a period ranging from 6 hours to 160 hours.

14. A metal or metal alloy plating bath comprising at least one source of metal ions which is characterised in that it comprises at least one imidazoyl urea polymer according to claim 1.

15. The metal or metal alloy plating bath according to claim 14 wherein the source of metal ions is a source of copper ions.

16. The metal or metal alloy plating bath according to claim 14 wherein the concentration of the at least one imidazoyl urea polymer in the metal or metal alloy plating bath ranges from 0.1 mg/L to 1000 mg/L.

17. The metal or metal alloy plating bath according to claim 15 wherein the concentration of the at least one imidazoyl urea polymer in the metal or metal alloy plating bath ranges from 0.1 mg/L to 1000 mg/L.

18. A method for deposition of metal or metal alloy onto a substrate comprising, in this order, the steps
   (i) providing a substrate,
   (ii) contacting the substrate with an aqueous metal or metal alloy plating bath according to claim 14, and
   (iii) applying an electrical current between the substrate and at least one anode, and thereby depositing a metal or metal alloy on at least a portion of the substrate.

19. The method of claim 18 wherein the substrate is selected from the group consisting of printed circuit boards, IC substrates, circuit carriers, interconnect devices, semiconducting wafers and glass substrates.

20. The method of claim 19 wherein the substrate have recessed structures selected from trenches, blind micro vias, through silicon vias and through glass vias.

21. A method for deposition of metal or metal alloy onto a substrate comprising, in this order, the steps
   (i) providing a substrate,
   (ii) contacting the substrate with an aqueous metal or metal alloy plating bath according to claim 15, and
   (iii) applying an electrical current between the substrate and at least one anode,
and thereby depositing a metal or metal alloy on at least a portion of the substrate.

* * * * *